United States Patent [19]

Stults et al.

[11] Patent Number: 5,185,451

[45] Date of Patent: Feb. 9, 1993

[54] BIS-IMIDES OF DIOXYDIPHTHALIC ACID

[75] Inventors: Jeffrey S. Stults; Willis T. Schwartz, both of Grand Island; Frank J. Dinan, Tonawanda, all of N.Y.

[73] Assignee: Occidental Chemical Corporation, Niagara Falls, N.Y.

[21] Appl. No.: 771,600

[22] Filed: Oct. 4, 1991

Related U.S. Application Data

[60] Continuation-in-part of Ser. No. 621,412, Dec. 3, 1990, Pat. No. 5,089,631, which is a division of Ser. No. 492,196, Mar. 13, 1990, Pat. No. 5,003,086, which is a division of Ser. No. 352,070, May 15, 1989, Pat. No. 4,943,642.

[51] Int. Cl.$^5$ .................. C07D 495/22; C07D 209/48
[52] U.S. Cl. ..................................... 548/418; 548/461
[58] Field of Search ........................... 548/418, 461

[56] References Cited

U.S. PATENT DOCUMENTS

| | | | |
|---|---|---|---|
| 3,746,721 | 7/1973 | Stephen | 548/461 |
| 3,879,428 | 4/1975 | Heath et al. | 548/461 |
| 4,697,023 | 9/1987 | Schwartz et al. | 549/241 |

FOREIGN PATENT DOCUMENTS 2416594  1/1975  Fed. Rep. of Germany .

OTHER PUBLICATIONS

Pebalk et al. *Chemical Abstracts* 88:135960a, p. 497, abstract of Dokl Akad Nauk SSSR 1977, 236(6), 1379–1382 (1978).

Tilika et al. *Chemical Abstracts* 97:55421u, p. 610, abstract of Latu. PSR Zinat Akad Vestic, Kim Ser (2), 201–204 (1982).

Pebalk et al. *Chemical Abstracts* 90:186029c, p. 585, abstract of Dokl. Akad. Nauk SSSR 1979 244(5) 1169–1173 (1979).

Kolesnikov, G. S. et al Vysokomol. Soyed, A9, 612–618 (1967).

Marvel, C. S. et al, J. Am. Chem. Soc., 80, 1197 (1958).

Lavrova, Z. N. et al, Volokna Sin. Polim., 15–24, (1970).

Erglis et al, CA 80(9):48007m, abstract of USSR Patent No. 395,358 (1974).

*Primary Examiner*—Richard L. Raymond
*Assistant Examiner*—Mark W. Russell
*Attorney, Agent, or Firm*—Wayne A. Jones; Arthur S. Cookfair

[57] ABSTRACT

Bis-imides of dioxydiphthalic or oxydiphthalic anhydride, are characterized by the formula

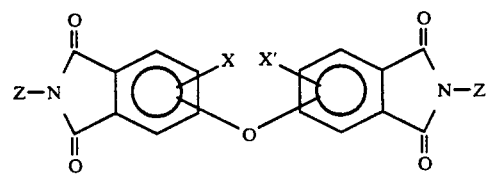

where Z is H, alkyl of 1–12 carbon atoms, or

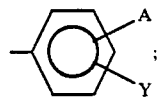

A is H, Cl, F, NO$_2$, OH, CF$_3$, alkyl, alkoxy, alkylaryl or aryloxy, wherein the alkyl groups are 1–6 carbon atoms and the aryl groups are 6–14 carbon atoms; alkenyl or alkynyl of 2–6 carbon atoms; or benzoyl; and Y is H, Cl, F, NO$_2$, OH, or CF$_3$; X is halogen; X' is hydrogen or halogen; or X and X' together represent an oxygen atom, forming a second ether linkage.

20 Claims, No Drawings

BIS-IMIDES OF DIOXYDIPHTHALIC ACID

BACKGROUND OF THE INVENTION

This is a Continuation-In-Part of application Ser. No. 07/621,412, filed Dec. 3, 1990 now U.S. Pat. No. 5,089,631; which is a Division of application Ser. No. 07/492,196, filed Mar. 13, 1990, now U.S. Pat. No. 5,003,086; which is a Division of application Ser. No. 07/352,070, filed May 15, 1989, now U.S. Pat. No. 4,943,642.

This invention relates to novel halo-oxydiphthalic and dioxydiphthalic bis-imide compounds. The products are useful chemical intermediates for the further preparation of various compounds and polymers, especially as monomers in the preparation of polyimides.

Kolesnikov, G.S. et al, *Vysokomol. Soyed*, A9, 612–18 (1967); Marvel, C.S. et al, *J. Am. Chem. Soc.*, 80, 1197, (1958); and Latrova, Z.N. et al, *Volokna Sin. Polim.*, 15–24 (1970), disclose the preparation of oxydiphthalic acids and anhydrides by the oxidation of tetramethyldiphenyl ethers.

U.S. Pat. No. 4,697,023 discloses the preparation of oxydiphthalic anhydrides and suggests their use in the preparation of polyimides. The oxydiphthalic anhydrides are prepared by the reaction of a halophthalic anhydride with water and an alkali metal compound such as KF, CsF, or $K_2CO_3$ in the presence of a polar aprotic solvent.

U.S. Pat. No. 3,879,428 to Heath et al discloses the preparation of various aromatic bis(ether anhydrides) by reaction of nitrophthalimide with an alkali diphenoxide followed by hydrolysis to yield the diether anhydride.

German Patent No. 2,416,594 (1975) discloses the preparation of oxydiphthalic anhydride by coupling of 3-nitrophthalic anhydride in the presence of metal nitrites such as sodium nitride.

Tilika et al, Synthesis of Carboxylic Acids of Aromatic Sulfides, Latv. PSR Zinat. Akad. Vestis, Kim. Ser. (2), 201–4, 1982; CA 97(7):55412U, disclose the reaction of 5-bromo-4-mercaptophthalic acid with $Cu_2O$ to give 80 percent thianthrene-2,3,7,8-tetracarboxylic acid, that is,

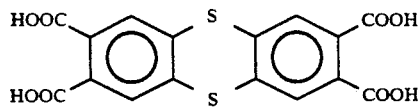

Pebalk et al, Spin Density Distribution In Anion Radicals of Aromatic Tetracarboxylic Acid Dianhydrides, Dokl. Akad. Nauk, SSR, 244(5), 1169–73, [Phys. Chem.] 1979; CA 90(23):186029c, disclose the EPR spectra of various compounds including a compound of the structure

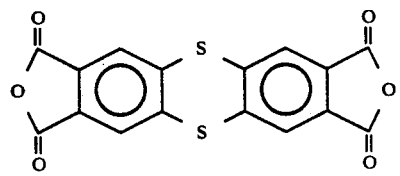

Pebalk et al, Electron-acceptor Properties of Aromatic Dianhydrides, Dokl. Akad. Nauk, SSR, 236(6), 1379–82, [Chem.] 1977; CA 88(19):135960a, disclose the electron-acceptor properties of 15 phthalic anhydrides and condensed phthalic anhydrides including dithiodiphthalic anhydrides.

2,3,7,8-Tetracarboxyphenoxathin dianhydride of the formula

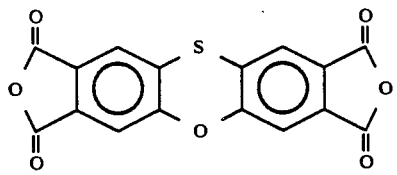

is disclosed by Erglis et al., (USSR Patent No. 395,358; CA 80(9):48007m). The compound was prepared by the reaction of $(3,4-Me_2C_6H_3)_2O$ with sulfur in the presence of aluminum chloride followed by oxidation with $KMnO_4$ in aqueous piperidine to form the tetracarboxylic acid, which was cyclized.

SUMMARY OF THE INVENTION

The present invention relates to new aromatic bis-imides of the formula

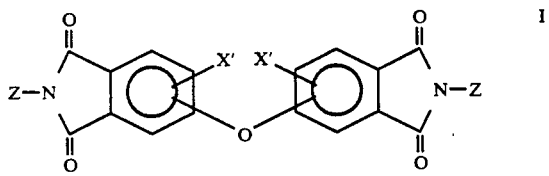

where Z is H, alkyl of 1–12 carbon atoms, or

Y is H, Cl, F, $NO_2$, OH, or $CF_3$; A is H, Cl, F, $NO_2$, OH, $CF_3$, alkyl, alkoxy, alkylaryl or aryloxy, wherein the alkyl groups are 1–6 carbon atoms and the aryl groups are 6–14 carbon atoms; alkenyl or alkynyl of 2–6 carbon atoms; or benzoyl; X is F, Cl, Br or I, X' is H, F, Cl, Br or I, or X and X' may together represent an oxygen atom forming a second ether linkage, with the proviso that when X and X' are taken together to represent an oxygen atom, the ether linkage is positioned at ring carbon sites adjacent to the sites forming the first ether linkage shown.

DETAILED DESCRIPTION OF THE INVENTION

The novel bis-imides of the above formula (I) may be prepared by reaction of the corresponding dianhydride with ammonia (to prepare the compound of Formula I wherein Z is hydrogen) or with an alkylamine or a suitably substituted aniline compound.

The halo-oxydiphthalic or dioxydiphthalic anhydride reactants used for the preparation of the bis-imides of Formula I can be prepared by reacting a dihalophthalic anhydride of the formula

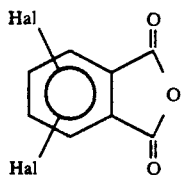

where Hal is F, Cl, Br or I with water and an alkali metal compound selected from the group consisting of KF, CsF, and K₂CO₃.

In the process, the halogen atoms on the dihalophthalic anhydride reactant function as leaving groups and become the site for the formation of an ether bridge. Thus, when the reactant is a 4,5-dihalophthalic anhydride such as

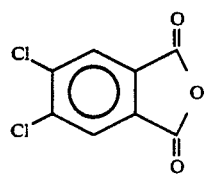

the reaction products will include 4,4'-dihalo-5,5'-oxydiphthalic anhydride, characterized by the formula

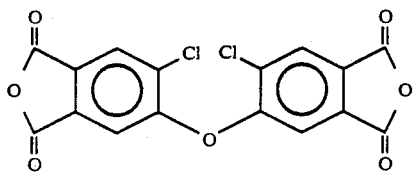

and 4,4',5,5'-dioxydiphthalic anhydride characterized by the formula

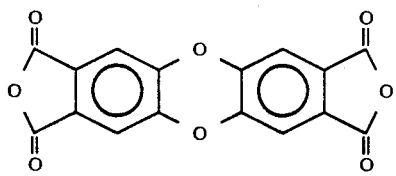

The particular halogen atoms at the 4 and 4' positions will depend on the halogen atoms present at the 4 or 5 position of the starting dihalophthalic anhydride. Thus, for example, the above dichloro-oxydiphthalic anhydride (IV) may be formed from 4,5-dichlorophthalic anhydride starting material. When difluorophthalic anhydride is employed, the corresponding difluoro-oxy-diphthalic anhydride may be formed. In addition, a mono-chloro-oxydiphthalic anhydride may be formed by using as a starting reactant a mixture of a monohalophthalic anhydride, such as 4-chlorophthalic anhydride and a dihalophthalic anhydride, such as 4,5-dichlorophthalic anhydride. Furthermore, the ring site of the oxygen bridge(s) may be varied by selective choice of the halophthalic anhydride reactant employed.

While not being bound by any particular theory, it is believed that the oxy-dihalo-diphthalic anhydride is formed as an intermediate during the initial stages of reaction. The percentage yield thereof may be enhanced by limiting the time of reaction. Alternatively, by increasing the reaction time, the dioxydiphthalic anhydride is produced essentially as the sole product. The halo-substituted oxydiphthalic anhydride is separable from the dioxydiphthalic anhydride by common physical separation means, such as selective recrystallization, etc. Fluoro-substituted bis-imides, prepared for example from difluoro-oxydiphthalic anhydride may be employed in the preparation of polyether imides having improved electrical properties, such as dielectric strength. In addition, the presence of fluorine ring substituents should increase the solubility of the polyimide in common solvents.

When the reactant is 3,4-dihalophthalic anhydride, the oxydiphthalic anhydride product formed will be 3,3',4,4'-dioxydiphthalic anhydride which, upon reaction with ammonia or an amine, will form a bis-imide characterized by the formula

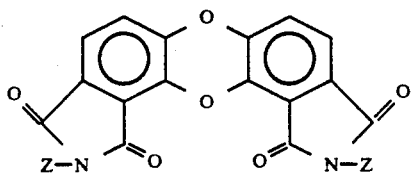

where Z is as defined above.

Alternatively, a mixture of the 3,4-dihalo- and 4,5-dihalo-phthalio anhydrides may be employed as the starting reactant to form a dioxydiphthalic anhydride which, upon reaction with ammonia or an amine, will form a bis-imide of the formula

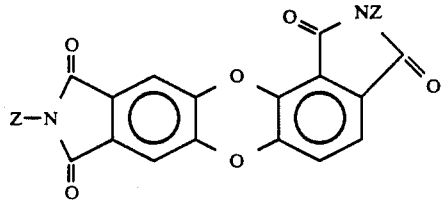

where Z is as defined above.

The halogen substituents on the starting halophthalic anhydride reactant may be F, Cl, Br or I. The preferred reactant is 4,5-dichlorophthalic anhydride.

The alkali metal compound may be potassium fluoride, cesium fluoride, or potassium carbonate, the latter being preferred. The proportions of reactants may vary considerably. However, it is recommended that the alkali metal compound be employed in sufficient proportions to provide at least two equivalents of potassium (or cesium) per mole of dihalophthalic anhydride. Preferably, the alkali metal compound is employed in substantial stoichiometric excess.

In the preparation of the halo-oxydiphthalic or dioxydiphthalic anhydride, water is a limiting reactant. Ideally, for maximum efficiency in the preparation of dioxydiphthalic anhydride, water is preferably present in a molar proportion of H₂O:dihalophthalic anhydride of about 1.0. The amount of halo-substituted oxydiphthalic anhydride produced can be increased by limiting the ratio of water to dihalophthalic anhydride to less than 1:1. The water may be added to the initial reaction mixture or alternatively, may be generated in situ. For example, when potassium carbonate is employed in the reaction mixture, a trace amount of water may be present in the initial reaction mixture and additional water generated in situ as the reaction proceeds.

The process is preferably carried out at atmospheric pressure, but super-atmospheric pressure, for example under autogenous conditions may be employed, if desired.

The process is preferably carried out neat. However, a solvent may be employed. The preferred solvents are polar, aprotic solvents such as N-methyl pyrrolidone, dimethyl formamide, dimethyl acetamide, triglyme, sulfolane, or the like, the most preferred solvent being sulfolane.

The temperature at which the process for the preparation of the dianhydride is carried out may vary considerably, but will generally be within the range of about 120° to about 230° C. Higher or lower temperatures may be employed, but are less preferred. If a solvent is employed, the choice of the solvent may govern the temperature employed. For example, at atmospheric conditions the boiling point of the solvent may become a limiting condition.

The dianhydride may be reacted with ammonia to form the corresponding ammonium phthalamate, heated to form diphthalamic acid, and dehydrated to yield the corresponding bis-imide. In a preferred embodiment, the dianhydride is reacted with an excess of concentrated ammonium hydroxide at reflux conditions to prepare the bis-ammonium phthalamate. The reaction mixture is then heated to remove water and excess ammonia. The phthalamic acid is then heated, preferably to at least 200° C., to form the bis-imide.

In the preparation of the substituted bis-imides of this invention, the diphthalic anhydride is reacted with an appropriately substituted amine, preferably in a molar ratio of amine:diphthalic anhydride of at least 2:1. The reaction may be carried out neat, but is preferably carried out in a solvent. The preferred solvents are polar, aprotic solvents such as N-methyl pyrrolidone, dimethyl formamide (DMF), dimethyl acetamide (DMAc), triglyme, sulfolane, or the like, the most preferred solvent being DMAc. The reaction is preferably carried out at a temperature of about 110° to 200° C., advantageously at reflux conditions. The reaction is typically carried out at atmospheric pressure. However, super-atmospheric or sub-atmospheric conditions may be employed, but are not generally preferred.

The bis-imides of the present invention are useful as monomers and/or additives in the formulation or preparation of various polymers. For example, the present bis-imides may be employed in the preparation of polyetherimides through an imide-amine exchange reaction catalyzed by a basic catalyst, such as an alkali metal or alkaline earth metal, or basic compounds thereof such as hydroxides, oxides, hydrides, carbonates and the like. In the process, a mixture of equal molar amounts of the dioxy diphthalic bis-imide of Formula 1 and an organic diamine are heated to the molten state, in the presence of the basic catalyst, to effect the imide-amine reaction. The process may be carried out under reduced pressure to facilitate the removal of the mono-organic amine and the formation of the polyetherimide. Suitable organic diamines include, for example, those of the formula NH$_2$-R-NH$_2$ where R is a divalent organic radical such as an alkylene or aromatic radical. Additional details regarding suitable diamines as well as suitable catalysts and general process conditions are set forth in U.S. Pat. No. 3,847,870.

In an alternate process, bis-imides compounds of the present invention such as compounds of Formula I, wherein Z is

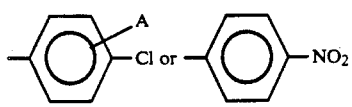

may be reacted with a dihydroxy compound, such as a diphenol or a bis-phenol compound to form a polyetherimide. For example, the bis-imide of Formula I where Z is

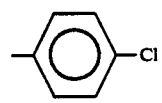

may be reacted with equal molar amounts of p-hydroxybenzophenone to form a poly(imide-ether-ketone).

In addition, the present bis-imides may be employed as plasticizers for organic polymers, such as polyvinylchloride and polyimides.

The following examples are provided to further illustrate the invention in the manner in which it may be carried out. It will be understood, however, that the specific details given in the examples have been chosen for purposes of illustration only and are not to be construed as limiting the invention. In the examples, unless otherwise indicated, all temperatures are in degrees Celsius.

EXAMPLE 1

Preparation of Dioxydiphthalic Anhydride

A solution of 21.7 grams (0.1 mole) of 4,5-dichlorophthalic anhydride in 40 grams of sulfolane was heated and maintained at 210°–215° C. while 0.215 grams of tetraphenylphosphonium bromide was added followed by the incremental addition of 13.82 grams (0.1 mole) of potassium carbonate over a period of about 4 hours. The temperature was maintained an additional hour and the reaction mixture was then cooled to room temperature. Acetone (100 ml) was added and mixed. The reaction mixture was filtered and the solids washed consecutively with another 100 ml of acetone, two 100 ml portions of water, and again with 100 ml of acetone, to yield about 15 grams of brown solid. After drying, the solid was recrystallized from about 225 grams of 1,2,4-trichlorobenzene to yield 12.5 grams of a tan colored crystalline solid. Mass spectral analysis indicated the product to have a molecular weight of 324 with a fragmentation consistent with dioxydiphthalic anhydride. The identification of dioxydiphthalic anhydride was confirmed by infra-red analysis and C$^{13}$ NMR (CP/MAS).

EXAMPLE 2

Preparation of Dioxydiphthalic Anhydride 4,5-Difluorophthalic anhydride (18.4 grams, 0.1 mole) was dissolved in 40 grams of anhydrous sulfolane and heated to 165° c. with stirring. Tetraphenylphosphonium bromide (0.184 grams, 0.0004 mole) and 1.8 grams (0.10 mole) of water were added and the temperature increased to 200° C. Anhydrous potassium fluoride (23.3 grams, 0.4 mole) was added with stirring. The reaction mixture was held at about 200° C. with stirring for about 3 ½ hours at which time another 0.2 grams of water was added and the reaction mixture was maintained at temperature for an additional hour. The reaction mixture was cooled to less than 150° C. and 35 grams of acetone added and the solids filtered off. The solids were washed with acetone followed by three 100 ml washes with distilled water. The solid material was dried at 150° C. for 16 hours to yield 15.5 grams (95.7% yield) of dioxydiphthalic anhydride.

EXAMPLE 3

Preparation of Dioxydiphthalic Acid

Dioxydiphthalic anhydride (3.0 g, 0.009 mole) was added to 95 g of water and heated to reflux. The dianhydride was dissolved by the addition of 4 ml of 40% NaOH. The resulting brown solution was decolorized with 0.2 g of activated carbon at reflux for 0.5 hour followed by filtration through celite. Acidifying with 12N HCl to a pH of less than 1 followed by a water wash and drying gave 1.9 g of product as confirmed by FTIR. DSC melting point was 260° C. with loss of water.

EXAMPLE 4

This example illustrates the manner in which chloro-oxydiphthalic anhydride may be prepared.

A solution of equal molar amounts of 4-chlorophthalic anhydride (18.2 g, 0.1 mole) and 4,5-dichlorophthalic anhydride (21.7 g, 0.1 mole) in 60 g of sulfolane is heated to 180°–210° C. Temperature is maintained, with stirring, while 0.05 mole (6.91 g) of potassium carbonate is added over a period of about one hour. The temperature is maintained for an additional two hours, then lowered to room temperature.

EXAMPLE 5

Potassium fluoride (5.04g) and Carbowax MPEG 2000 (0.71 g) were added to and mixed with 10.2 g of a mixture of 56.1% (GC are percent) 4,5-difluorophthalic anhydride and 43.9% (GC area percent) 4-chloro-5-fluorophthalic anhydride. The powdery mixture was heated in a flask to 180° C., forming a viscous, paste-like reaction mixture. The temperature was maintained at 180°–207° C. for approximately 3.5 hours, during which a portion of the reaction mixture sublimed and condensed on the upper portion of the flask. The flask was cooled to room temperature and the sublimate collected (6.69 g) and analyzed by gas chromatography, indicating, in area percent, 74% 4,5-difluorophthalic anhydride and 26% 4-chloro-5-fluorophthalic anhydride. The reaction mixture remaining at the bottom of the flask (7.58 g) was analyzed by gas chromatography and found to contain in area percent, 50.1% 4,5-difluorophthalic anhydride; 42.8% 4-chloro-5-fluorophthalic anhydride; 3.4% 4,4'-difluoro-5,5'-oxydiphthalic anhydride; 2.1% 4-chloro-4'-fluoro-5,5'-oxydiphthalic anhydride; 0.3% 4,4'-dichloro-5,5'-oxydiphthalic anhydride and 1.0% 4,4',5,5'-dioxydiphthalic anhydride.

EXAMPLE 6

Preparation of Bis-imide of Dioxydiphthalic Anhydride

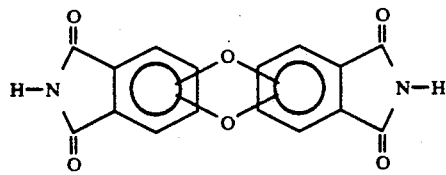

Dioxydiphthalic anhydride (6.52 g, 0.0020 mole) was added to 200 ml of concentrated ammonium hydroxide in a round bottom flask fitted with a reflux condenser. The mixture was heated to reflux over a period of about one-half hour during which the mixture turned dark brown in color. The reflux condenser was removed from the reaction flask and, with continued heating, most of the remaining liquid was removed, to leave an olive-green solid. The solid was dried and mixed with N,N-dimethylacetamide (DMAc) and the mixture heated to reflux to form an amber solution. The solution was treated with decolorizing carbon, filtered, and cooled to form white crystals. The crystals were washed with acetone and dried to yield a final product (5.25 g, 81% yield) in the form of pale yellow crystals (M.P. = >400° C.)

EXAMPLE 7

Preparation of Bis(N-p-hydroxyphenyl)imide of dioxydiphthalic Anhydride

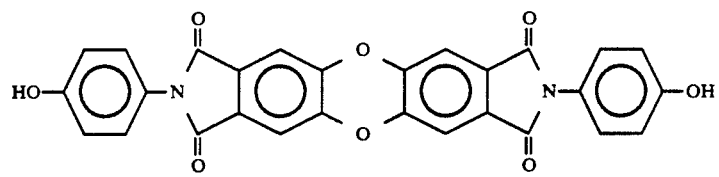

To 1.20 g (0.11 mole) of 4-aminophenol in 50 mL of DMAc was added 1.62 g (0.003 mole) of dioxydiphthalic anhydride. The mixture was refluxed under an atmosphere of nitrogen for 3.5 hours. The resulting slurry was filtered, washed with acetone, and dried, to yield 2.13 g (90% yield) of white crystals which, upon heating, exhibited charring at about 400° C.

EXAMPLE 8

Preparation of Bis(N-p-chlorophenyl)imide of Dioxydiphthalic Anhydride

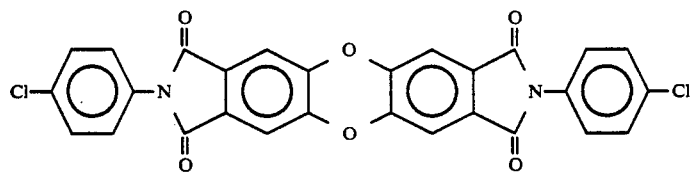

To 1.40 g (0.009 mole) of 4-chloroaniline in 50 mL of DMAc was added 1.62 g (0.003 mol) of dioxydiphthalic anhydride. The mixture was refluxed for 19 hours under an atmosphere of nitrogen, and the resulting slurry was filtered, rinsed with acetone, and dried to yield 2.1 g (84% yield) of bis-N-p-chlorphenyl)imide of dioxydiphthalic anhydride as yellow crystals (M.P. >400° C.)

EXAMPLE 9

Preparation of Bis(N-p-fluorophenyl)imide of Dioxydiphthalic Anhydride

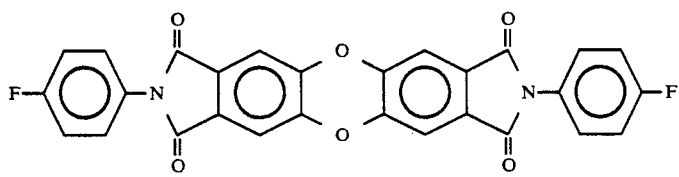

The bis-N-p-fluorophenyl)imide of dioxydiphthalic anhydride is prepared following the general procedure of Example 8, except that in place of 4-chloroaniline, there is substituted a molar equivalent amount of 4-fluoroaniline.

EXAMPLE 10

Preparation of the Bis(N-p-nitrophenyl)imide of Dioxydiphthalic Anhydride

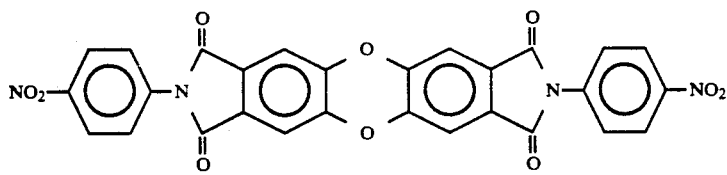

To 1.52 g (0.011 mole) of 4-nitroaniline in 50 mL of DMAc, was added 1.62 g (0.003 mole) of dioxydiphthalic anhydride. The mixture was refluxed under a nitrogen atmosphere for two hours. The resulting slurry was filtered and rinsed with acetone to yield 1.4 g of yellow solid (51% yield). Upon heating, charring occurred at about 400° C.

The bis(N-p-nitrophenyl)imide of dioxydiphthalic anhydride, prepared in accordance with Example 10, may be reduced to the diamine by reduction with hydrogen over Pd/C in DMAc.

EXAMPLE 11

Preparation of Bis(N-p-aminophenyl)imide

The bis(N-nitrophenyl)imide prepared in accordance with Example 10 is dissolved in a solvent, such as DMAc, and reduced with hydrogen over Pd/C to form the corresponding diamine.

EXAMPLE 12

Preparation of the Bis(N-p-trifluoromethylphenyl)imide of Dioxydiphthalic Anhydride

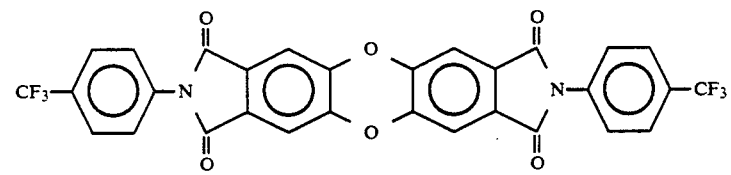

The bis(N-p-trifluoromethylphenyl)imide of dioxydiphthalic anhydride is prepared following the general procedure of Example 10, except that, in place of 4-nitroaniline, there is substituted an equivalent molar amount of 4-trifluoromethylaniline.

EXAMPLE 13

Preparation of the N-phenyl Bis-imide of Dioxydiphthalic Anhydride

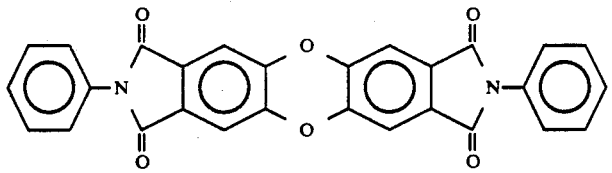

To 1.03 g (0.01 mole) of aniline in 50 mL of DMAc was added 1.62 g (0.003 mole) of dioxydiphthalic anhydride. The mixture was refluxed, under nitrogen, for two hours. The resulting slurry was filtered and washed with acetone and dried.

What is claimed is

1. An oxydiphthalic bis-imide compound of the formula

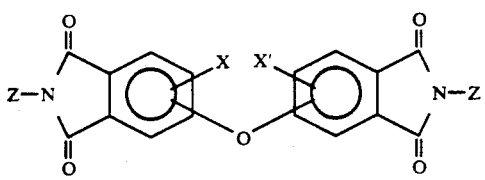

where Z is H, alkyl of 1-12 carbon atoms, or

Y is H, Cl, F, $NO_2$, OH, $CF_3$, alkyl, alkoxy, alkylaryl or aryloxy, wherein the alkyl groups are 1-6 carbon atoms and the aryl groups are 6-14 carbon atoms; alkenyl or alkynyl or 2-6 carbon atoms; or benzoyl; A is H, Cl, F, $NO_2$, OH, or $CF_3$; X is F, Cl, Br or I, X' is H, F, Cl, Br or I, or X and X' taken together represent an oxygen atom forming a second ether linkage, with the proviso that when X and X' are taken together to represent an oxygen atom, the other linkage is positioned at ring carbon sites adjacent to the ring carbon sites of the first ether linkage, and with the further proviso that both A and Y cannot be in a position ortho to the carbon-nitrogen bond of the imide.

2. A compound according to claim 1 wherein X is F, Cl, or Br and X' is H, F, Cl or Br.

3. A compound according to claim 1 wherein X and X' together represent an oxygen atom.

4. A compound according to claim 1 wherein Z is H.

5. A compound according to claim 3 wherein Z is H.

6. A compound according to claim 3 wherein Z is

where A is Cl, F, $NO_2$, OH, or $CF_3$; and Y is Cl, F, $NO_2$, OH, or $CF_3$.

7. A compound according to claim 6 wherein A is H.

8. A compound according to claim 7 wherein Y is Cl.

9. A compound according to claim 7 wherein Y is F.

10. A compound according to claim 7 wherein Y is $NO_2$.

11. A compound according to claim 7 wherein Y is OH.

12. A compound according to claim 7 wherein Y is $CF_3$.

13. A compound of the formula

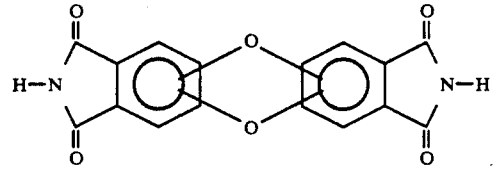

14. A compound of the formula

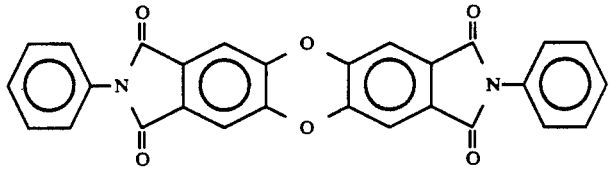

15. A compound of the formula

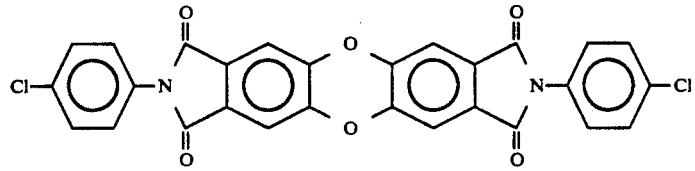

16. A compound of the formula

17. A compound of the formula
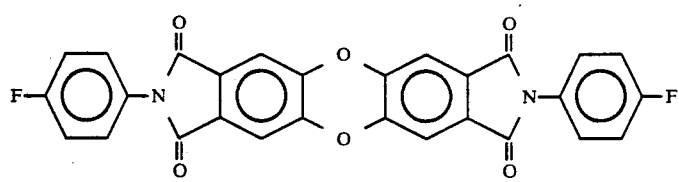
18. A compound of the formula
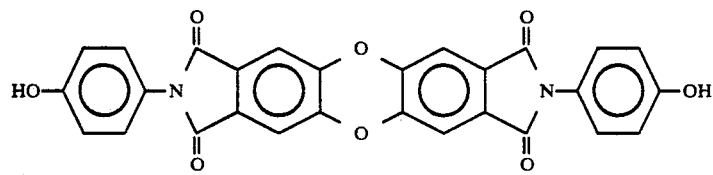
19. A compound of the formula
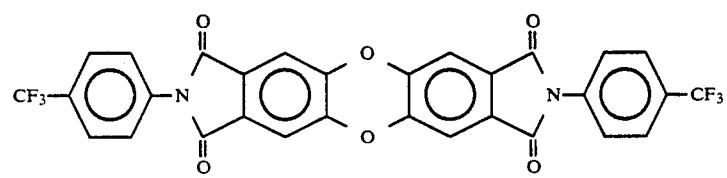
20. A compound of the formula
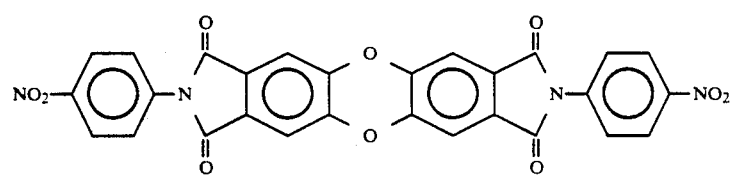
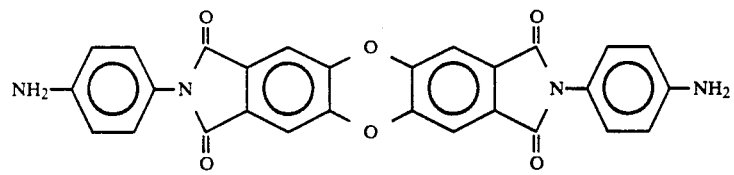
* * * * *